United States Patent
Krishnan et al.

(10) Patent No.: US 10,851,388 B2
(45) Date of Patent: Dec. 1, 2020

(54) TISSUE SELECTIVE TRANSGENE EXPRESSION

(71) Applicant: GENOME BIOLOGICS UG, Frankfurt am Main (DE)

(72) Inventors: Jaya Krishnan, Frankfurt am Main (DE); Jonathan Ward, Wetzikon (CH)

(73) Assignee: GENOME BIOLOGICS UG, Frankfurt am Main (DE)

( * ) Notice: Subject to any disclaimer, the term of this patent is extended or adjusted under 35 U.S.C. 154(b) by 35 days.

(21) Appl. No.: 15/775,030

(22) PCT Filed: Nov. 10, 2016

(86) PCT No.: PCT/EP2016/077351
§ 371 (c)(1),
(2) Date: May 10, 2018

(87) PCT Pub. No.: WO2017/081204
PCT Pub. Date: May 18, 2017

(65) Prior Publication Data
US 2018/0334686 A1    Nov. 22, 2018

(30) Foreign Application Priority Data

Nov. 11, 2015 (EP) .................................. 15194155
May 11, 2016 (EP) .................................. 16169261

(51) Int. Cl.
| | | |
|---|---|---|
| *C12N 15/86* | (2006.01) | |
| *C12N 15/11* | (2006.01) | |
| *C12N 15/85* | (2006.01) | |
| *A01K 67/027* | (2006.01) | |
| *C12Q 1/6888* | (2018.01) | |

(52) U.S. Cl.
CPC .......... *C12N 15/86* (2013.01); *A01K 67/0275* (2013.01); *C12N 15/111* (2013.01); *C12N 15/85* (2013.01); *C12Q 1/6888* (2013.01); *A01K 2217/05* (2013.01); *A01K 2227/105* (2013.01); *C12N 2310/14* (2013.01); *C12N 2320/12* (2013.01); *C12N 2750/14143* (2013.01); *C12N 2800/30* (2013.01); *C12N 2830/008* (2013.01); *C12Q 2600/124* (2013.01); *C12Q 2600/158* (2013.01)

(58) Field of Classification Search
CPC ..................................................... C12N 15/86
See application file for complete search history.

(56) References Cited

FOREIGN PATENT DOCUMENTS

| JP | 2009189318 | 8/2009 |
|---|---|---|
| WO | WO9827207 | 6/1998 |
| WO | WO03096969 | 11/2003 |

OTHER PUBLICATIONS

Orban et al. (1992, PNAS, vol. 89, pp. 6861-6854) (Year: 1992).*

* cited by examiner

*Primary Examiner* — Thaian N. Ton
*Assistant Examiner* — David A. Montanari
(74) *Attorney, Agent, or Firm* — JMB Davis Ben-David

(57) ABSTRACT

A method for expression of transcribable unit(s) in a target cell is provided. The method comprises the steps of: a) providing a target cell expressing a site-specific recombinase, b) providing a DNA vector characterized by a 5' to 3' vector sequence orientation. The DNA vector comprises a plurality of recombination units, wherein a single recombination unit comprises at least one transcribable unit and a first type and a second type of target site that are recognizable by the site-specific recombinase. Recombination can only occur between two target sites of the same type and the first type of target site is located at the 5' start of the recombination unit and the second type of target site is located at the 3' end of the recombination unit. For all recombination units comprised within the DNA vector, the orientation of all of the first type of target sites are the same, and the orientation of all of the second type of target sites are the same. Step c) comprises introducing the DNA vector into the target cell.

Figure 1:
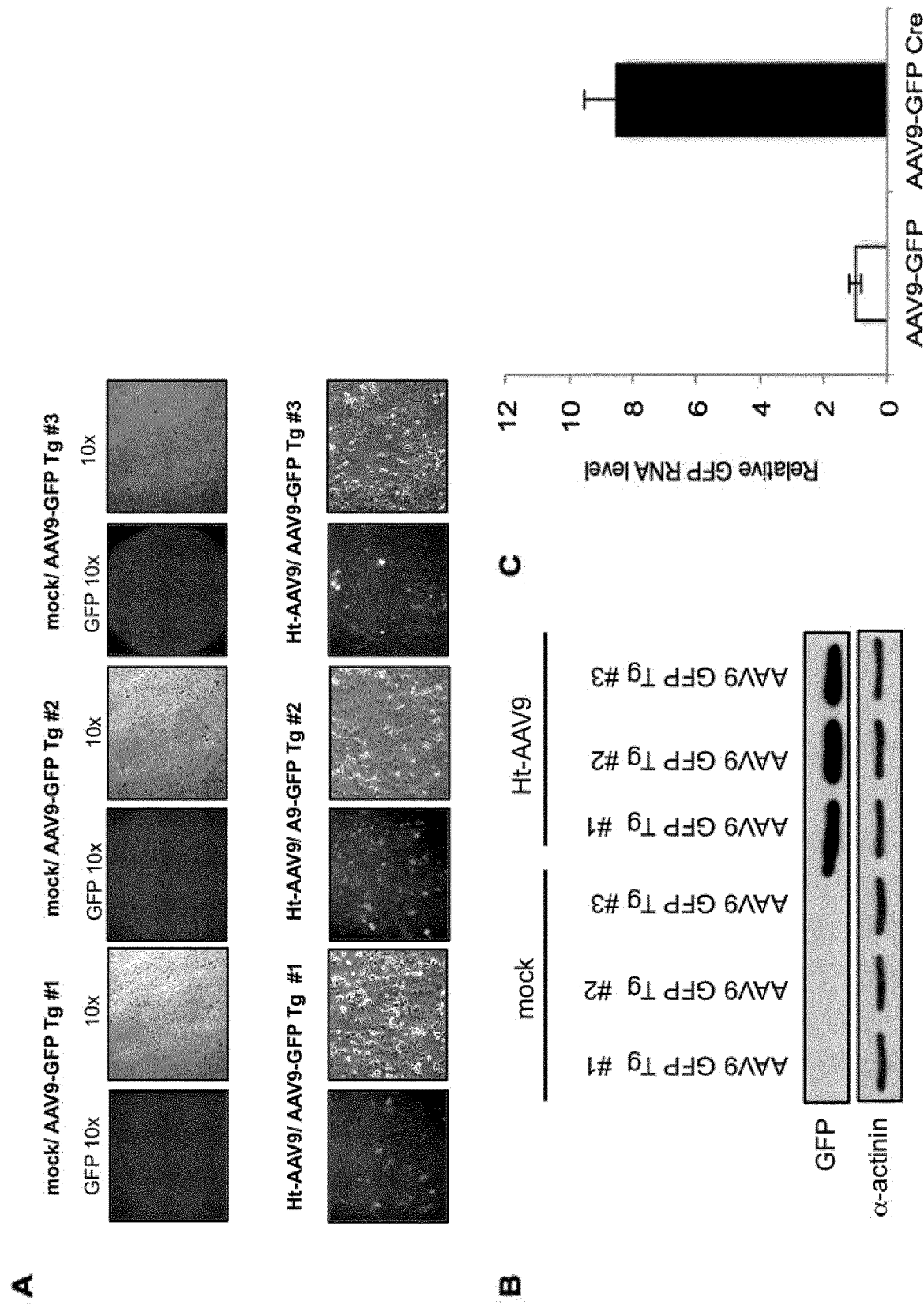

10 Claims, 8 Drawing Sheets
Specification includes a Sequence Listing.

TISSUE SELECTIVE TRANSGENE EXPRESSION

CROSS-REFERENCE TO RELATED APPLICATIONS

This is the U.S. National Stage of International Patent Application No. PCT/EP2016/077351 filed Nov. 10, 2016, which was published in English under PCT Article 21(2), and which in turn claims the benefit of European Patent Application Nos. 15194155.6 filed Nov. 11, 2015 and 16169261.1 filed May 11, 2016.

FIELD OF THE INVENTION

The present invention relates to a method for tissue specific expression of randomly selected transcribable units.

BACKGROUND OF THE INVENTION

For the past two decades, in vivo validation of gene function in adult mammals has necessitated the generation of novel animal lines, specific for each gene studied. This laborious, time-consuming and costly procedure entails the generation of targeting vectors specific for the gene (or locus) of interest, the low efficiency transduction and homologous recombination of the targeting vector in embryonic stem (ES) cells, the subsequent screening of ES cell clones for single-copy homologous recombination events and the generation of founder animals to identify a single effective strain. When coupled to Cre-lox methodologies to enable tissue-specific and/or inducible-gene expression or inactivation, the time required for the generation of effective strains is further lengthened by the need to establish mice homozygous for the transgene of interest, and carrying an additional wild type or mutant Cre recombinase transgene, conferring tissue-specific and/or inducibility of gene expression. In its totality, the time taken to generate a novel rodent line wherein a specific gene is either ectopically expressed or inactivated, in a tissue-specific or inducible manner in the adult, takes approximately two to three years. Although developments in CRISPR/Cas technology has led to increased transgenesis efficiency, the need to expand animal populations after generation of novel mouse lines remains time consuming. This bottleneck dramatically impedes research and lengthens the time required to validate the in vivo relevance of a gene or mechanistic pathway in normal physiology or in disease processes (Kumar et al., Methods Mol Biol 590, 335-362, 2009).

To circumvent these issues, a variety of virus-based approaches have been developed involving the delivery of adenoviruses, adeno-associated viruses (AAV) or lentiviruses directly to specific organs by surgical or invasive techniques, or through systemic viral delivery. Although some viral subtypes, such as adenoviruses and lentiviruses, exhibit a degree of tropism towards specific organs when delivered systemically or provide an acceptable level of infectivity and gene transduction when delivered using invasive methods to specific organs, adenoviruses and lentiviruses are not effective platforms for general tissue-targeting strategies in adult rodents. In contrast, AAVs delivered systemically exhibit tropism towards a broad range of organs. In particular, the AAV subtype 9 has been shown to exhibit multi-organ infectivity with a high efficiency of gene transduction (Lotze and Kost, Cancer Gene Ther 9, 692-699, 2002; Naldini et al., Science, 1996).

The multi-organ tropism exhibited by AAV however, precludes the analysis and understanding of gene or pathway function in an organ- or context-specific manner (Inagaki et al., Mol Ther 14, 45-53, 2006).

The problem underlying the present invention is to provide the means for long term tissue specific in vivo expression of transcribable units without the need for the generation of transgenic animals for each transcribable unit. This problem is solved by the subject-matter of the independent claims.

SUMMARY OF THE INVENTION

According to a first aspect of the invention, a method for expression of transcribable unit(s) in a target cell is provided. The method comprises the steps of
  providing a target cell expressing a site-specific recombinase,
  providing at least one or more DNA vectors characterized by a 5' to 3' vector sequence orientation, wherein
  the at least one DNA vector or each of the DNA vectors comprises independently from each other a plurality of recombination units, and wherein a single recombination unit comprises at least one transcribable unit and a first type and a second type of target site both recognizable by the site-specific recombinase, and wherein:
    recombination can only occur between two target sites of the same type;
    the first type of target site is located at the 5' start of the recombination unit and the second type of target site is located at the 3' end of the recombination unit;
    for all recombination units comprised within the DNA vector, the orientation of all of the first type of target sites are the same, and the orientation of all of the second type of target sites are the same;
  introducing the at least one DNA vector or the DNA vectors into the target cell.

According to a second aspect of the invention, a DNA vector is provided. The DNA vector comprises:
  a plurality of recombination units, wherein a single recombination unit comprises at least one transcribable unit and a first type and a second type of target site both recognizable by the site-specific recombinase, and wherein:
    recombination can only occur between two target sites of the same type;
    the first type of target site is located at the 5' start of the recombination unit and the second type of target site is located at the 3' end of the recombination unit;
    for all recombination units comprised within the DNA vector, the orientation of all of the first type of target sites are the same, and the orientation of all of the second type of target sites are the same.

According to a third aspect of the invention, a method for in vivo assessment of a plurality of transcribable units for phenotype variation in a tissue of interest is provided. The method comprises the steps of:
  in vivo expression of at least one transcribable unit in a tissue of interest according to the method of the first aspect of the invention,
  harvesting of the tissue of interest,
  separating of the tissue of interest into individual cells and sorting of the individual cells according to a phenotype of interest,
  identifying the transcribable unit(s) expressed in each of the sorted individual cells, relating the transcribable unit(s) to the phenotype of interest of the individual cells.

According to a fourth aspect of the invention, a transgenic animal is provided. The transgenic animal is characterized by a genetic locus comprising:

a plurality of recombination units, wherein a single recombination unit comprises at least one transcribable unit and a first type and a second type of target site both recognizable by a site-specific recombinase, and wherein:

recombination can only occur between two target sites of the same type;

said first type of target site is located at the 5' start of said recombination unit and said second type of target site is located at the 3' end of said recombination unit;

for all recombination units comprised within said DNA vector, the orientation of all of said first type of target sites are the same, and the orientation of all of said second type of target sites are the same.

According to a fifth aspect of the invention, a method for generating a transgenic animal is provided. The method comprises the use of a DNA vector comprising:

a plurality of recombination units, wherein a single recombination unit comprises at least one transcribable unit and a first type and a second type of target site both recognizable by a site-specific recombinase, and wherein:

recombination can only occur between two target sites of the same type;

said first type of target site is located at the 5' start of said recombination unit and said second type of target site is located at the 3' end of said recombination unit;

for all recombination units comprised within said DNA vector, the orientation of all of said first type of target sites are the same, and the orientation of all of said second type of target sites are the same.

According to a sixth aspect of the invention a transgenic animal is provided obtainable by a method according to the fifth aspect of the invention.

SPECIFIC DESCRIPTION OF THE INVENTION

According to a first aspect of the invention, a method for expression of transcribable unit(s) in a target cell is provided. The method comprises the steps of providing a target cell expressing a site-specific recombinase, providing a DNA vector characterized by a 5' to 3' vector sequence orientation, wherein the DNA vector comprises a plurality of recombination units, and wherein a single recombination unit comprises at least one transcribable unit and a first type of target site and a second type of target site (of a specific sequence identical for all target sites of a given type of target site recognized by the recombinase) recognizable by the site-specific recombinase, and wherein:

recombination can only occur between two target sites of the same type;

the first type of target site is located at the 5' start of the recombination unit followed by a transcribable unit, and the second type of target site is located in 3' position of the transcribable unit closest to the 3' end of the recombination unit with the transcribable unit(s) being located between the two types of target sites;

for all recombination units comprised within the DNA vector, the orientation of all of the first type of target sites are the same, and the orientation of all of the second type of target sites are the same;

no other target sites recognized by the site specific recombinase are present on the DNA vector;

introducing the DNA vector into the target cell.

Without wishing to be bound by theory, the inventors postulate that recombination of the DNA vector by binding of the site-specific recombinase to the target sites comprised within the expression vector, yields a recombined DNA vector comprising a single recombination unit selected from the plurality of recombination units.

In the context of the present specification, the term site-specific recombinase (SSR) is used in its meaning known in the field of molecular biology and molecular genetics. It refers to enzymes that catalyse directionally sensitive DNA exchange reactions between short (usually 30-40 nucleotides) directional target site sequences that are specific to each site-specific recombinase. Although a given SSR can recognizes different target sites, only between identical target sites recombination occurs. The DNA exchange reactions include excision/insertion and inversion of the DNA between the target sites. The type of DNA exchange reaction catalysed depends on the relative orientation of the target sites. When two target sites are oriented in the same direction, SSR excises the DNA flanked by the target sites, leaving a single target site behind. Conversely, when the two target sites are oriented in different directions, SSR flips the flanked DNA into the antisense orientation. After excision of the DNA flanked by target sites half of each target site remains thereby forming a new target site of the same type and orientation.

In certain embodiments, the target cell is a eukaryotic cell. In certain embodiments, the target cell is a cell of a multicellular organism. In certain embodiments, the target cell is a non-human cell. In certain embodiments, the target cell is a mammalian cell. In certain embodiments, the targeting cell is a mammalian cell, provided that the target cell is not a human cell.

In certain embodiments, the recombination unit comprises 2 to 25 transcribable units, in particular 5 to 20 transcribable units, more particular 10 to 15 transcribable units.

In certain embodiments, the plurality of recombination units comprises 2 to 80 recombination units, in particular 5 to 60 recombination units, more particular 10 to 50 recombination units.

In certain embodiments, the plurality of recombination units comprises 3 to 80 recombination units.

In the context of the present specification the terms expressing or expression are used in their meaning known in molecular biology and genetics; they refer to the process by which information from a nucleic acid sequence is used in the synthesis of a functional product. The functional product can be a protein or a functional RNA including non-coding RNA (ncRNA), short-hairpin RNA (shRNA), small interfering RNA (siRNA) or micro RNA (miRNA).

In certain embodiments, each of the recombination units in the DNA vector additionally comprises a transcriptional terminator located between the transcribable unit closest to the 3' end of the recombination unit and the second type of target site.

In certain embodiments, the DNA vector additionally comprises two transcribable units not being part of a recombination unit.

In certain embodiments, the DNA vector additionally comprises two transcribable units not being part of a recombination unit, wherein one of those transcribable units is in 5'-position of the first recombination unit and the other transcribable unit is in 3'-position of the last recombination unit. Such additional transcribable units may serve as controls. One such example of a control would be a non-silencing shRNA.

In certain embodiments, the DNA vector additionally comprises two transcribable units not being part of a recombination unit, wherein one of those transcribable units is in 5'-position of the first recombination unit and encodes a first non-silencing shRNA, and the other transcribable unit is in 3'-position of the last recombination unit and encodes a second non-silencing shRNA.

In certain embodiments, the target cells expressing the site-specific recombinase are comprised within or constitutes a tissue of interest in a living organism.

In certain embodiments, the tissue of interest is selected from heart, liver, brain, kidney, testes, muscle and adipose tissue.

In certain embodiments, the site-specific recombinase is selected from Cre-recombinase and FLP.

In certain embodiments, the Cre-recombinase is selected from YP_006472.1, YP_008494422.1 (entries in the NCBI Protein Database https://www.ncbi.nlm.nih.gov/protein) and gene homologs thereof.

In certain embodiments, the FLP recombinase is selected from NP_040495.1, NP_040496.1 1 (entries in the NCBI Protein Database https://www.ncbi.nlm.nih.gov/protein) and gene homologs thereof. In certain embodiments, FLP recombinase is encode by a nucleic acid characterized by

```
                                            SEQ ID NO 005
(ATGGCTCCTAAGAAGAAGAGGAAGGTGATGAGCCAGTTCGACATCCTGT

GCAAGACCCCCCCCAAGGTGCTGGTGCGGCAGTTCGTGGAGAGATTCGAG

AGGCCCAGCGGCGAGAAGATCGCCAGCTGTGCCGCCGAGCTGACCTACCT

GTGCTGGATGATCACCCACAACGGCACCGCCATCAAGAGGGCCACCTTCA

TGAGCTACAACACCATCATCAGCAACAGCCTGAGCTTCGACATCGTGAAC

AAGAGCCTGCAGTTCAAGTACAAGACCCAGAAGGCCACCATCCTGGAGGC

CAGCCTGAAGAAGCTGATCCCCGCCTGGGAGTTCACCATCATCCCTTACA

ACGGCCAGAAGCACCAGAGCGACATCACCGACATCGTGTCCAGCCTGCAG

CTGCAGTTCGAGAGCAGCGAGGAGGCCGACAAGGGCAACAGCCACAGCAA

GAAGATGCTGAAGGCCCTGCTGTCCGAGGGCGAGAGCATCTGGGAGATCA

CCGAGAAGATCCTGAACAGCTTCGAGTACACCAGCAGGTTCACCAAGACC

AAGACCCTGTACCAGTTCCTGTTCCTGGCCACATTCATCAACTGCGGCAG

GTTCAGCGACATCAAGAACGTGGACCCCAAGAGCTTCAAGCTGGTGCAGA

ACAAGTACCTGGGCGTGATCATTCAGTGCCTGGTGACCGAGACCAAGACA

AGCGTGTCCAGGCACATCTACTTTTTCAGCGCCAGAGGCAGGATCGACCC

CCTGGTGTACCTGGACGAGTTCCTGAGGAACAGCGAGCCCGTGCTGAAGA

GAGTGAACAGGACCGGCAACAGCAGCAGCAACAAGCAGGAGTACCAGCTG

CTGAAGGACAACCTGGTGCGCAGCTACAACAAGGCCCTGAAGAAGAACGC
```

```
CCCCTACCCCATCTTCGCTATCAAGAACGGCCCTAAGAGCCACATCGGCA

GGCACCTGATGACCAGCTTTCTGAGCATGAAGGGCCTGACCGAGCTGACA

AACGTGGTGGGCAACTGGAGCGACAAGAGGGCCTCCGCCGTGGCCAGGAC

CACCTACACCCACCAGATCACCGCCATCCCCGACCACTACTTCGCCCTGG

TGTCCAGGTACTACGCCTACGACCCCATCAGCAAGGAGATGATCGCCCTG

AAGGACGAGACCAACCCCATCGAGGAGTGGCAGCACATCGAGCAGCTGAA

GGGCAGCGCCGAGGGCAGCATCAGATACCCCGCCTGGAACGGCATCATCA

GCCAGGAGGTGCTGGACTACCTGAGCAGCTACATCAACAGGCGGATCTG
```

A) (Raymond & Soriano (2007) PLoS ONE, 2(1), e162).

In certain embodiments, the site-specific recombinase is a Cre-recombinase, and the sequence of the target site (5'-3' orientation) is selected from

```
                                            SEQ ID NO 001
    (ATAACTTCGTATAGCATACATTATACGAAGTTAT)
    and

SEQ ID NO 002
    (ATAACTTCGTATAGGATACTTTATACGAAGTTAT).
```

In certain embodiments, the site-specific recombinase is a FLP-recombinase, and the sequence of the target site (5'-3' orientation) is selected from

```
                                            SEQ ID NO 003
    (TGAAGTTCCTATACTTTCTAGAGAATAGGAACTTC)
    and

SEQ ID NO 004
    (GAAGTTCCTATTCTCTAGAAAGTATAGGAACTTCA).
```

In certain embodiments, expression of the site-specific recombinase is under control of an inducible promoter.

In certain embodiments, the method of the invention comprises the steps of:
  providing a target cell expressing a site-specific recombinase,
  providing a plurality of DNA vectors characterized by a 5' to 3' vector sequence orientation, wherein
    each of the DNA vectors of the plurality comprises independently from each other a plurality of recombination units, and wherein a single recombination unit comprises at least one transcribable unit and a first type and a second type of target site both recognizable by the site-specific recombinase, and wherein:
      recombination can only occur between two target sites of the same type;
      the first type of target site is located at the 5' start of the recombination unit and the second type of target site is located at the 3' end of the recombination unit;
      for all recombination units comprised within the DNA vector, the orientation of all of the first type of target sites are the same, and the orientation of all of the second type of target sites are the same;
  introducing the plurality of DNA vectors into the target cell.

In certain embodiments, the plurality of DNA vectors comprises 2 to 10 DNA vectors, particularly 3 to 5 DNA vectors.

In certain embodiments, the DNA vector comprises a multitude of selection units, wherein each of the selection units comprises:
a promoter to enable expression of the transcribable units within the target cell, in particular an U6 promoter, and
a multitude of recombination units.

Particularly, by using a multitude of selection units in the DNA vector, for each selection unit one transcribable unit will be expressed after recombination. For example, using three selection units with 10 transcribable units each would result in the expression of three transcribable units (one for each selection unit) that are randomly selected from the 10 transcribable units comprised within the respective selection units.

In certain embodiments, the multitude of selection units comprises 2 to 50 selection units. In certain embodiments, the multitude of selection units comprises 3 to 30 selection units. In certain embodiments, the multitude of selection units comprises 5 to 20 selection units.

In certain embodiments, the multitude of recombination units comprised within a selection unit of the multitude of selection units comprises 2 to 50 recombination units. In certain embodiments, the multitude of recombination units comprised within a selection unit of the multitude of selection units comprises 3 to 30 recombination units. In certain embodiments, the multitude of recombination units comprised within a selection unit of the multitude of selection units comprises 5 to 20 recombination units. In certain embodiments, the multitude of recombination units comprised within a selection unit of the multitude of selection units comprises 5 to 10 recombination units.

In certain embodiments, the selection units are on different DNA-vectors. This embodiment is advantageous for the use of a large number of transcribable units or transcribable units with long sequences to avoid size limitations of the DNA vector used.

In certain embodiments, each of the transcribable units comprised within the DNA vector is independently of each other selected from ncRNA, shRNA, siRNA, miRNA and protein coding sequence. In other words, the DNA vector may contain a combination of each type of transcribable unit.

In certain embodiments, the transcribable unit is a Green fluorescent protein (GFP) coding sequence.

In certain embodiments, the DNA vector is an expression vector.

In certain embodiments, the DNA vector is an expression vector, particularly a viral vector derived from a virus selected from adeno-associated virus, adenovirus, lentivirus, retrovirus and baculovirus.

In certain embodiments, the DNA vector is a viral vector derived from a virus selected from adeno-associated virus, adenovirus, lentivirus, retrovirus and baculovirus.

In certain embodiments, the target cell is expressing at least two site-specific recombinases not being able to recognize target sites of the other site-specific recombinase. In certain embodiments, the DNA vector comprises a first type and a second type of target site specific for each site-specific recombinase. Each selection unit comprises a promoter and a multitude of recombination units comprising only target sites (first and second type) specific for one of the site-specific recombinases. By combining selection units comprising target sites for different site-specific recombinases no recombination events can take place between different selection units.

According to a second aspect of the invention a DNA vector is provided. The DNA vector comprises:
a plurality of recombination units, wherein a single recombination unit comprises at least one transcribable unit and a first type and a second type of target site both recognizable by a site-specific recombinase, and wherein:
recombination can only occur between two target sites of the same type;
the first type of target site is located at the 5' start of the recombination unit and the second type of target site is located at the 3' end of the recombination unit;
for all recombination units comprised within the DNA vector, the orientation of all of the first type of target sites are the same, and the orientation of all of the second type of target sites are the same;
no other target sites recognized by the site-specific recombinase are present on the DNA vector.

In the context of the present specification, the term DNA vector is used in its meaning known in the art of molecular biology; it refers to a DNA molecule used as a vehicle to carry genetic material into another cell. DNA vectors include, without being limited to, plasmids and viral vectors. Commonly used types of DNA vectors include expression vectors and DNA constructs used for the generation of transgenic animals.

In certain embodiments, the plurality of recombination units comprises 2 to 80 recombination units, in particular 5 to 60 recombination units, more particular 10 to 50 recombination units. In certain embodiments, the plurality of recombination units comprises 3 to 80 recombination units.

In certain embodiments, each of the recombination units in the DNA vector additionally comprises a transcriptional terminator located between the transcribable unit closest to the 3' end of the recombination unit and the second type of target site.

In certain embodiments, the DNA vector additionally comprises a promoter to enable expression of the transcribable units, particularly an U6 promoter.

In certain embodiments, the DNA vector additionally comprises two transcribable units not being part of a recombination unit.

In certain embodiments, the DNA vector comprises a multitude of selection units, wherein each of the selection units comprises:
a promoter to enable expression of the transcribable units, in particular U6 promoter, and
a multitude of recombination units.

In certain embodiments, the multitude of selection units comprises 2 to 50 selection units. In certain embodiments, the multitude of selection units comprises 3 to 30 selection units. In certain embodiments, the multitude of selection units comprises 5 to 20 selection units.

In certain embodiments, the multitude of recombination units comprised within a selection unit of the multitude of selection units comprises 2 to 50 recombination units. In certain embodiments, the multitude of recombination units comprised within a selection unit of the multitude of selection units comprises 3 to 30 recombination units. In certain embodiments, the multitude of recombination units comprised within a selection unit of the multitude of selection units comprises 5 to 20 recombination units. In certain embodiments, the multitude of recombination units comprised within a selection unit of the multitude of selection units comprises 5 to 10 recombination units.

In certain embodiments, the DNA vector additionally comprises two transcribable units not being part of a recombination unit, wherein one of those transcribable units is in 5'-position of the first recombination unit and the other transcribable unit is in 3'-position of the last recombination unit. Such additional transcribable units may serve as controls. One such example of a control would be a non-silencing shRNA.

In certain embodiments, the DNA vector additionally comprises two transcribable units not being part of a recombination unit, wherein one of those transcribable units is in 5'-position of the first recombination unit and encodes a first non-silencing shRNA, and the other transcribable unit is in 3'-position of the last recombination unit and encodes a second non-silencing shRNA.

In certain embodiments, each of the transcribable units comprised within the DNA vector is independently of each other selected from ncRNA, shRNA, siRNA, miRNA and protein coding sequence. In other words, a DNA vector may contain a combination of each type of transcribable unit.

In certain embodiments, the transcribable unit is a Green fluorescent protein (GFP) coding sequence.

In certain embodiments, the DNA vector is an expression vector.

In certain embodiments, the DNA vector is a viral vector derived from a virus selected from adeno-associated virus, adenovirus, lentivirus, retrovirus and baculovirus.

In certain embodiments, the DNA vector is an expression vector, particularly a viral vector derived from a virus selected from adeno-associated virus, adenovirus, lentivirus, retrovirus and baculovirus.

Particularly, such DNA vector may be used to generate transgenic animals, particularly transgenic mice.

In certain embodiments, the DNA vector additionally comprises DNA sequences homologous to DNA sequences in a locus of interest comprised within an organism to be transformed or transfected by the DNA vector of the invention, thereby facilitating homologous recombination with the locus of interest. In certain embodiments, the locus of interest is the ROSA26 locus.

According to a third aspect of the invention, a method for in vivo assessment of a plurality of transcribable units for phenotype variation in a tissue of interest is provided. The method comprises the steps of:
  in vivo expression of at least one transcribable unit in a tissue of interest according to the method of the first aspect of the invention, yielding a tissue of interest comprising a plurality of cell populations, wherein all cells of one cell population are expressing the same transcribable unit(s),
  harvesting of said tissue of interest,
  separating of the tissue of interest into individual cells and sorting of the individual cells according to a phenotype of interest,
  identifying the transcribable unit expressed in each of the sorted individual cells,
  relating the transcribable unit to the phenotype of interest of the individual cells.

In certain embodiments, the phenotype of interest is cell size, cell morphology, cell staining or a cell marker. Cell staining is to be understood in this context as any feature of a cell that can either be directly stained with an appropriate dye or is indirectly stained by affinity binders (e.g. antibodies, aptamers) that are coupled to a dye or appropriate marker. Methods known in the art for the sorting of cells due to cell size, cell morphology or cell staining include flow cytometry, in particular fluorescence-activated cell sorting (FACS).

In certain embodiments, the tissue of interest is a non-human tissue.

According to a fourth aspect of the invention, a transgenic animal is provided. The transgenic animal is characterized by a genetic locus comprising:
  a plurality of recombination units, wherein a single recombination unit comprises at least one transcribable unit and a first type and a second type of target site both recognizable by a site-specific recombinase, and wherein:
    recombination can only occur between two target sites of the same type;
  said first type of target site is located at the 5' start of said recombination unit and said second type of target site is located at the 3' end of said recombination unit, wherein particularly said transcribable unit is located between said first type and said second type of target site;
  for all recombination units comprised within said DNA vector, the orientation of all of said first type of target sites are the same, and the orientation of all of said second type of target sites are the same.

In the context of the present specification, the term genetic locus is used in its meaning known in the field of molecular biology and molecular genetics. It refers to the specific location of a DNA sequence in the genome. In organisms having a multitude of chromosomes, the genetic locus determines a specific position on one of the chromosomes. One example of a genetic locus commonly used in the generation of transgenic mice, where the introduced DNA sequence is constitutively and ubiquitously expressed, is the ROSA26 locus.

In certain embodiments, the plurality of recombination units comprises 2 to 80 recombination units, in particular 5 to 60 recombination units, more particular 10 to 50 recombination units. In certain embodiments, the plurality of recombination units comprises 3 to 80 recombination units.

In certain embodiments, the transgenic animal is a mammal, in particular, a pig, a sheep or a rodent, more particularly a rabbit, a mice or a rat.

In certain embodiments, the transgenic animal expresses a site-specific recombinase being able to recognize the first type and the second type of target site comprised within a single recombination unit of the above described plurality of recombination units. In certain embodiments, a nucleic acid molecule comprised within the transgenic animal and encoding the site-specific recombinase is under transcriptional control of an inducible promoter operable in the transgenic animal.

According to a fifth aspect of the invention, a method for generating a transgenic animal is provided. The method comprises the use of a recombinant non-naturally occurring DNA vector comprising:
  a plurality of recombination units, wherein a single recombination unit comprises at least one transcribable unit and a first type and a second type of target site both recognizable by a site-specific recombinase, and wherein:
    recombination can only occur between two target sites of the same type;
  said first type of target site is located at the 5' start of said recombination unit, and said second type of target site is located at the 3' end of said recombination unit, wherein particularly said transcribable unit is located between said first type and said second type of target site;
  for all recombination units comprised within said DNA vector, the orientation of all of said first type of target sites are the same, and the orientation of all of said second type of target sites are the same.

Particularly, the generated transgenic animal comprises the above described plurality of recombination units.

In certain embodiments, the plurality of recombination units comprises 2 to 80 recombination units, in particular 5 to 60 recombination units, more particular 10 to 50 recombination units. In certain embodiments, the plurality of recombination units comprises 3 to 80 recombination units.

In certain embodiments, the transgenic animal is a mammal, in particular, a pig, a sheep or a rodent, more particularly a rabbit, a mice or a rat.

In certain embodiments, the DNA vector is used for homologous recombination of embryonic stem cells used for the generation of the transgenic animal.

In certain embodiments, the DNA vector is used for pronuclear injection to generate transgenic animals.

In certain embodiments, the DNA sequence comprised in the DNA vector is introduced into the genome of the transgenic animal by the use of CRISPR/CAS or ZFN (zinc finger nuclease) technology.

In certain embodiments, the generated transgenic animal is crossed with an animal expressing a site-specific recombinase being able to recognize the first type and the second type of target site comprised within a single recombination unit of the above described plurality of recombination units.

According to a sixth aspect of the invention, a transgenic animal is provided obtainable by a method according to the fifth aspect of the invention.

Wherever alternatives for single separable features such as, for example, an isotype protein or phenotype, type of expression vector or transcribable unit are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

SHORT DESCRIPTION OF THE FIGURES

FIG. 1 shows neonatal mouse cardiomyocytes (NMC) that were infected with AAV9-MLC2v-lox-STOP-lox-GFP-transgene in triplicate, in the absence (top panels) or presence (lower panels) of ectopic Cre recombinase (Ht-AAV9) (A). Samples from (A) were further assessed for GFP by immunoblotting (B) and qPCR (C) (p<0.005). Sarcomeric α-actinin serves as a loading control for immunoblotting in (B) and GFP expression, as assayed by qPCR, was normalised to hypoxanthine guanine phosphoribosyl transferase (Hprt) (p<0.005).

Figure 2:
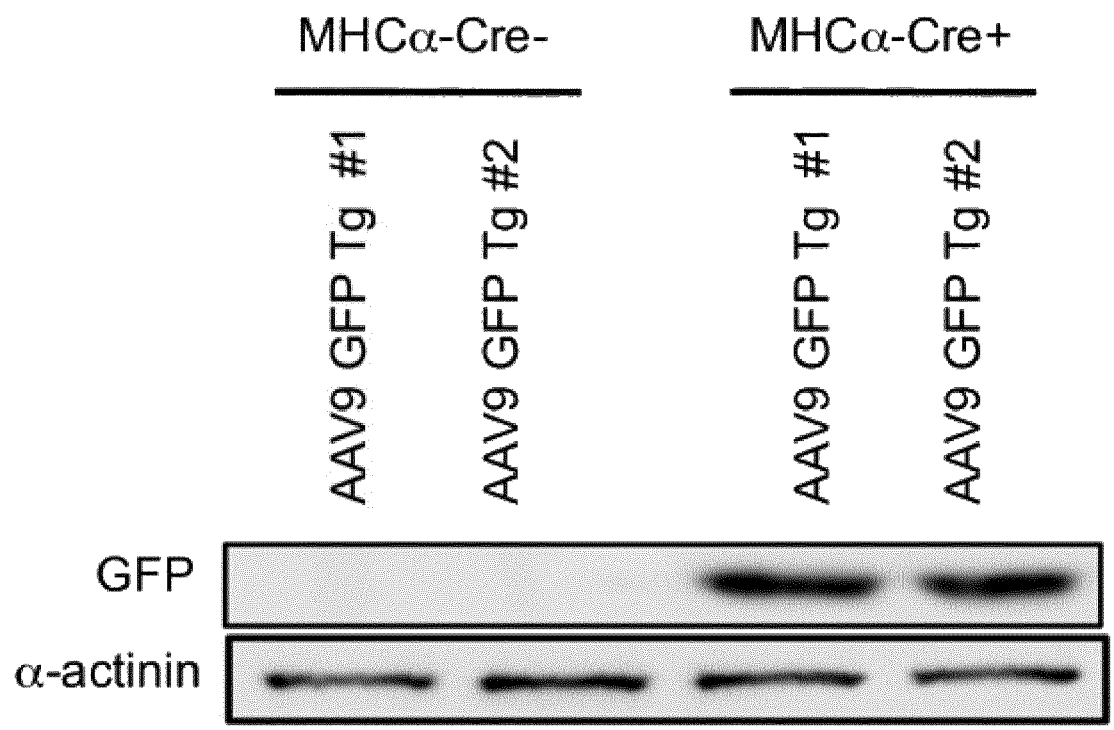

FIG. 2 shows tail-vein injection of AAV9-MLC2v-lox-STOP-lox-GFP into MHCα-driven tamoxifen inducible Cre-recombinase mice, in the absence (Cre−) or presence (Cre+) of tamoxifen-mediated Cre recombinase activation. GFP expression in vivo was validated by immunoblotting for GFP, with sarcomeric α-actininin as a loading control. Protein lysates derived from two independent experiments are shown for the respective sets.

Figure 3:
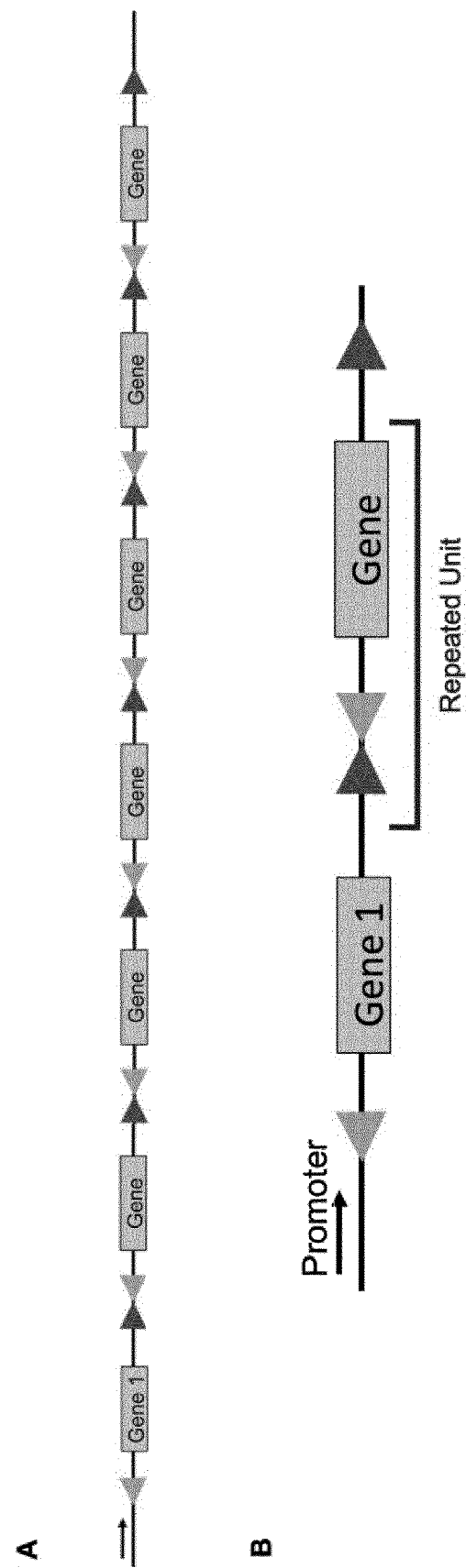

FIG. 3 shows the schematic of an AAV construct for simultaneous organ-specific multi-transgenesis. Arrow indicates upstream PolIII promoter, with red and green triangles indicating loxP elements in a convergent or divergent orientation, respectively. Blue squares indicate the position of transgenes within the construct (A). The minimal repetitive unit of the construct is shown in (B).

Figure 4:
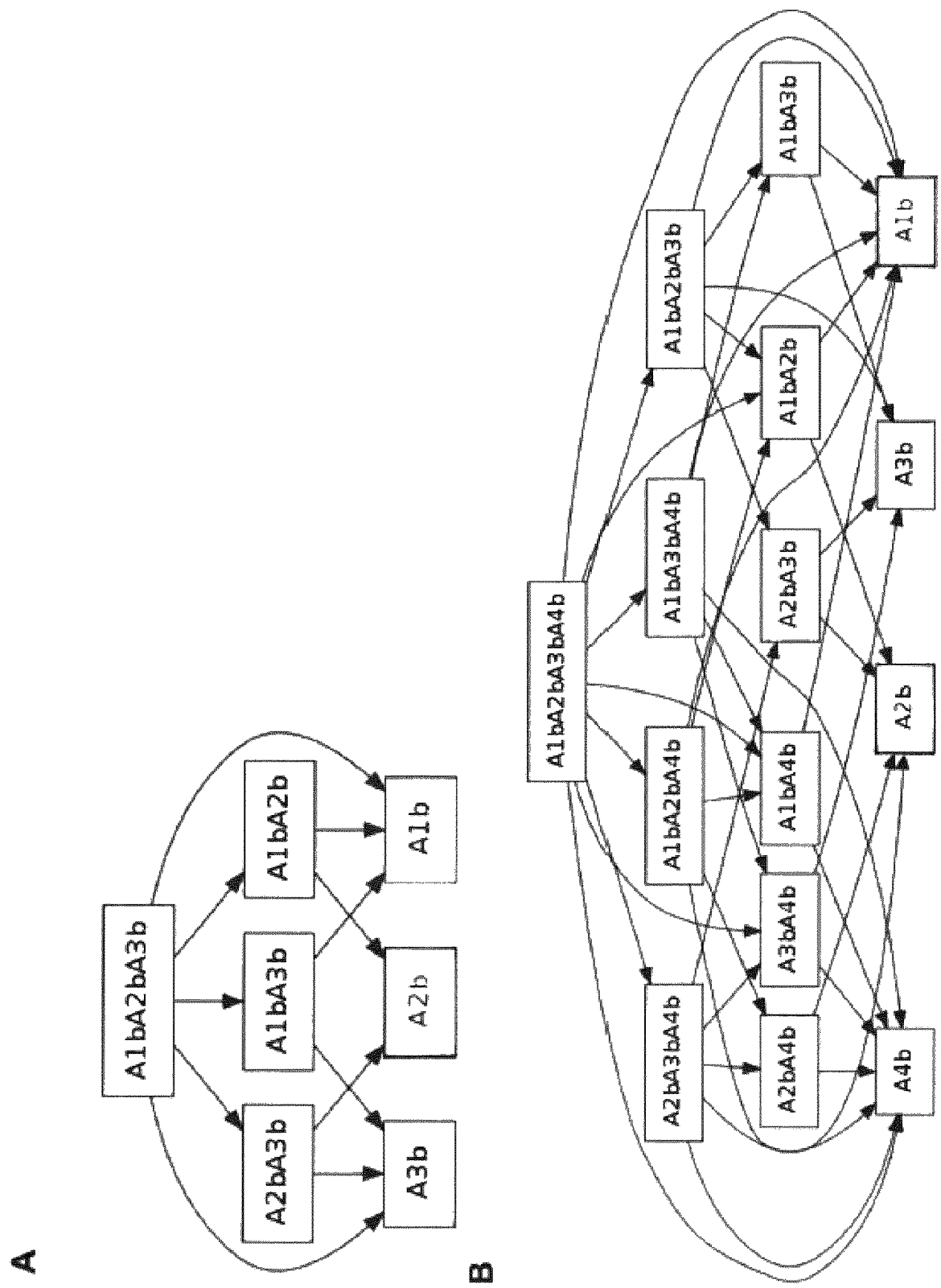

FIG. 4 shows a schematic representation of excision events leading to the presence of a single transcriptionally active transgene unit downstream of the promoter for a construct harbouring three individual transgenes (A) and four individual transgenes (B). 'A' indicates loxP element in convergent orientation, while 'b' indicates loxP element in a divergent orientation. Numbers in the respective boxes refer to the individual transgenes.

Figure 5:
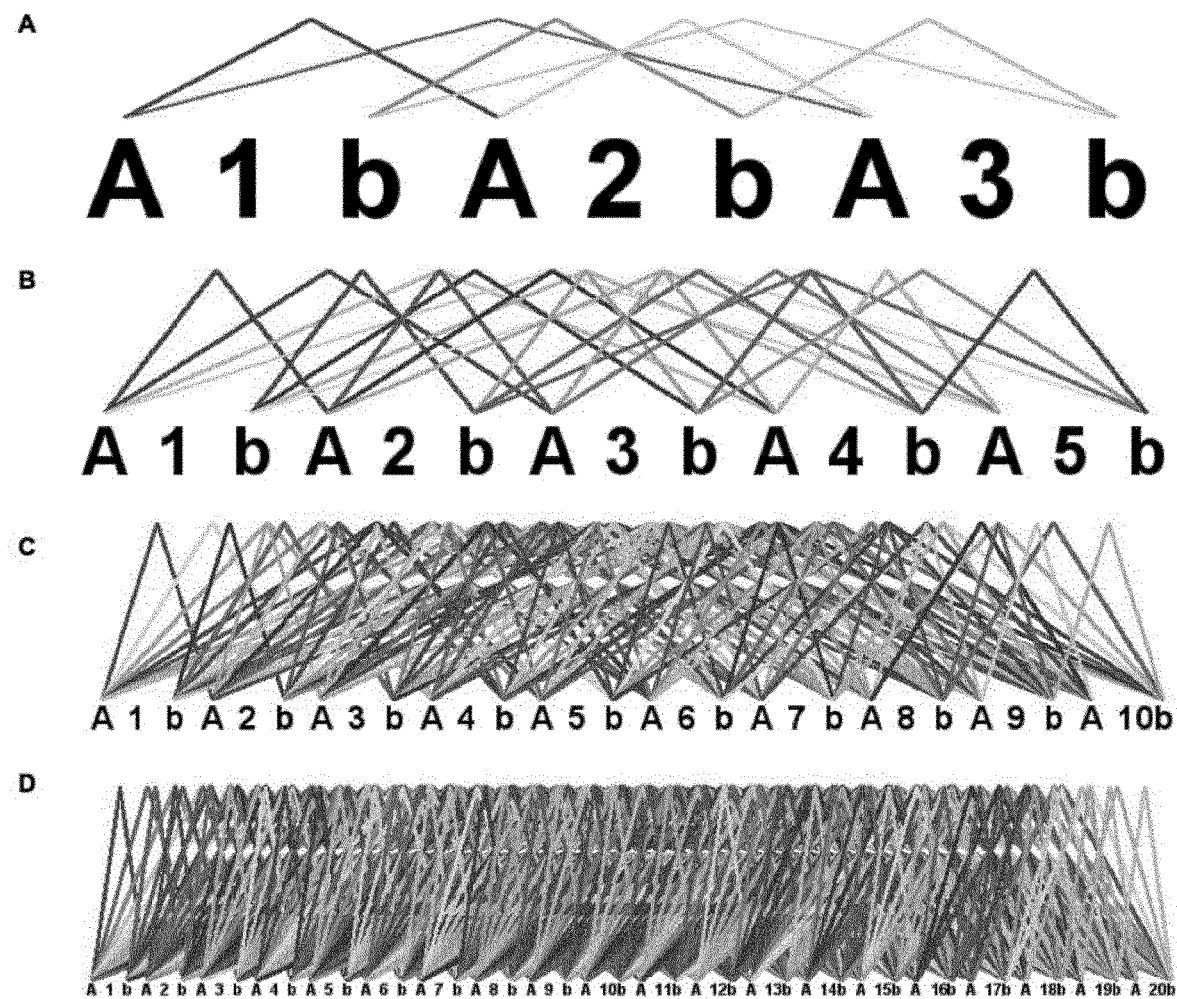

FIG. 5 shows a schematic representation of the series of excision events leading to the presence of a single transcriptionally active transgene unit downstream of the promoter for a construct harbouring three (A), five (B), ten (C) or twenty individual transgenes (D). 'A' indicates loxP element in convergent orientation, while 'b' indicates loxP element in a divergent orientation. Numbers refer to individual transgenes.

Figure 6:
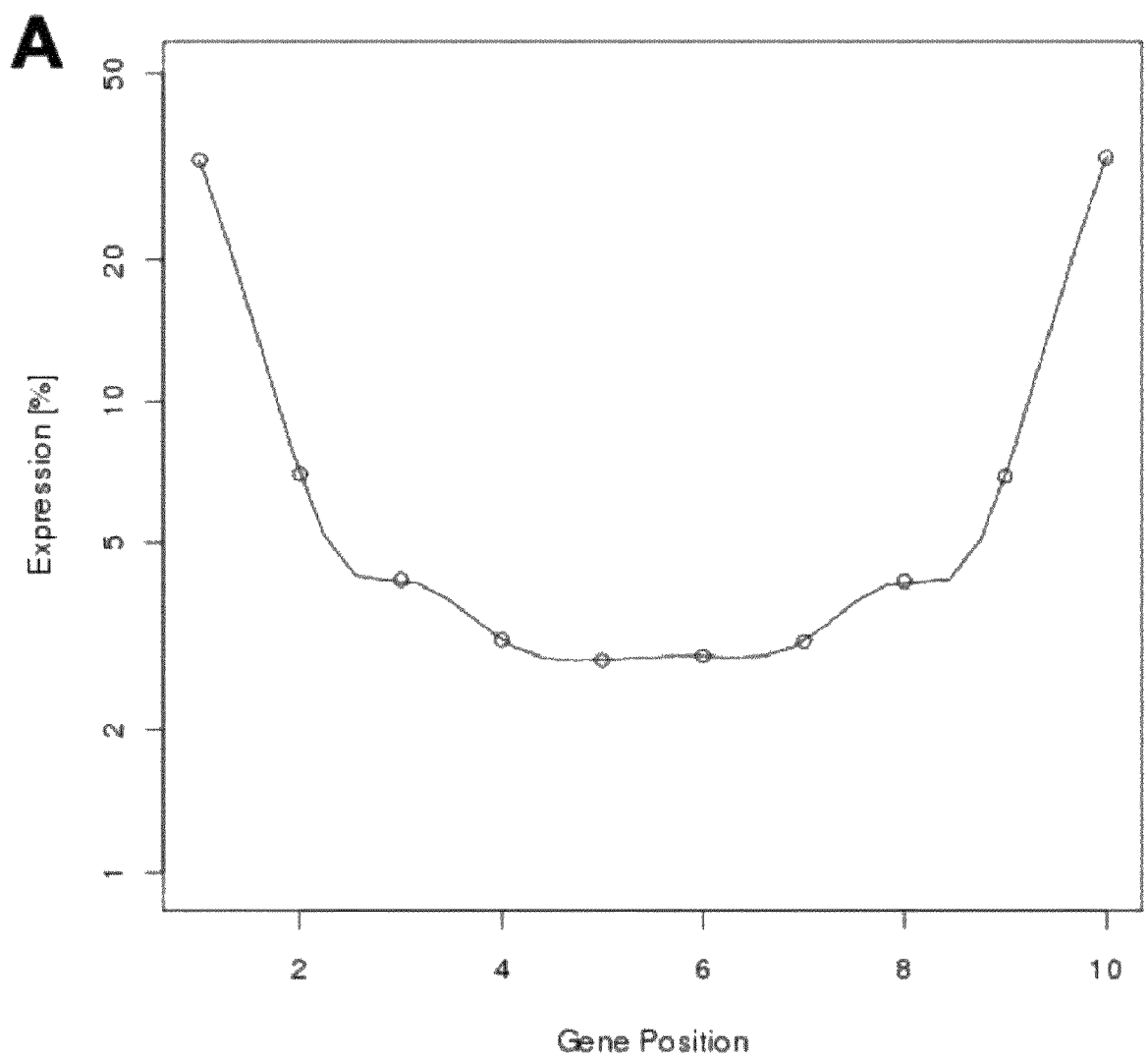
Figure 6:
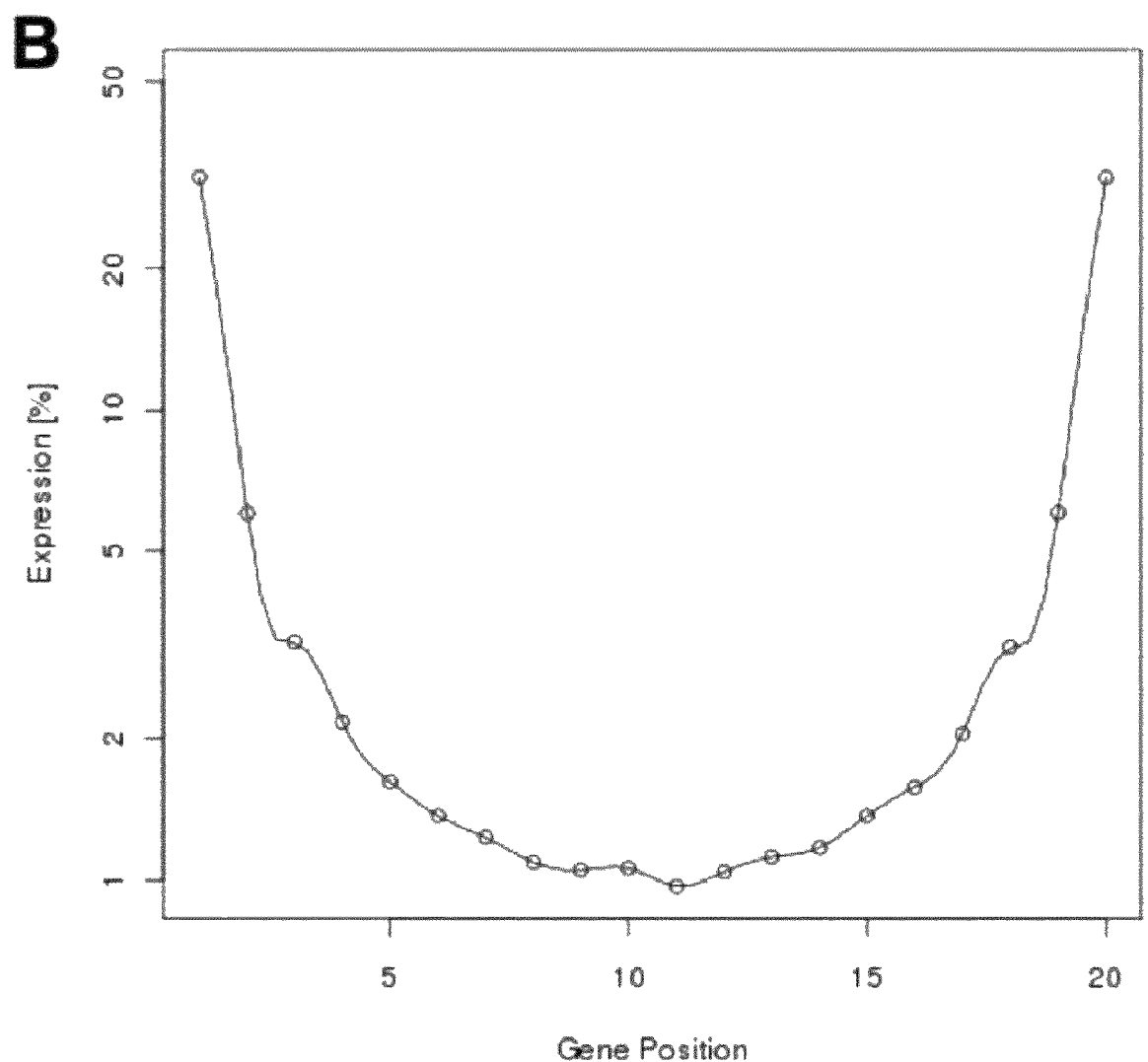
Figure 6:
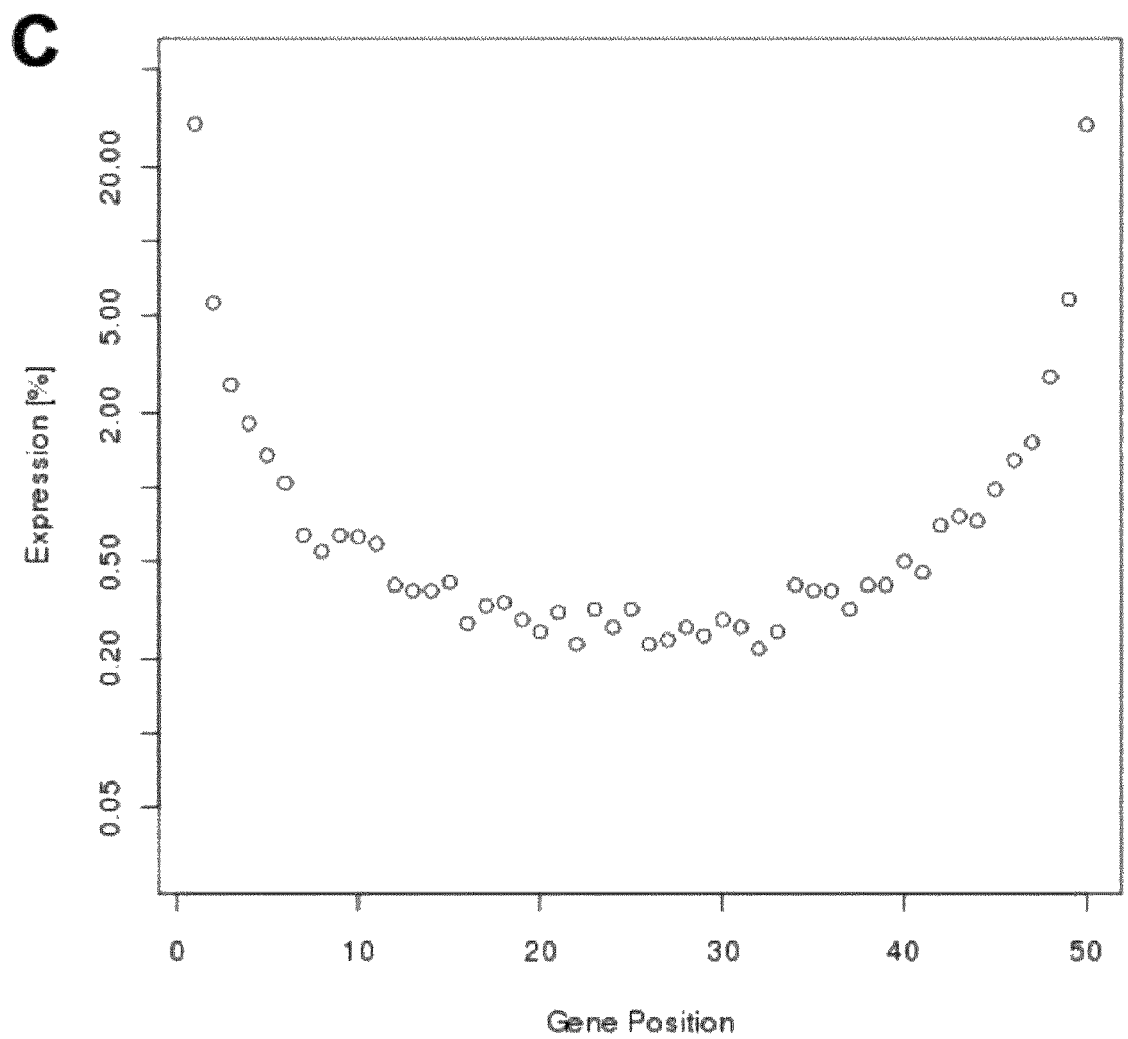

FIG. 6 shows the distribution of transgene expression from a 10 (A), 20 (B) and 50 (C) transgene AAV construct. Expression percentage (y-axis) indicates percentage of cardiomyocytes expressing the respective transgene. The x-axis shows position of the transgene with the respective AAV constructs.

EXAMPLES

In order to overcome the above mentioned drawbacks of known methodology, the inventors have developed a novel AAV-based strategy for tissue-specific, inducible and long-term animal transgenesis. By virtue of the broad tropism of viral vectors such as AAV, this system allows for the specific targeting of multiple organs, including the brain, kidney, liver, spleen, adipose tissue, skeletal muscle and the heart. Importantly, this approach potentially allows for the high-throughput analysis of in vivo organ-specific gene function directly in animals, without the need to generate a new line of transgenic animals for each gene analyzed.

This approach entails the generation of an AAV harbouring the transgene combination of interest, downstream of an RNA polymerase II (RNA PolII)- or RNA polymerase III (RNA PolIII)-driven promoter. When delivered systemically into adult rodents harbouring the cardiac-specific myosin heavy chain (MHC) α-driven tamoxifen inducible Cre-recombinase (Cre), the AAV9 virus is transduced to a number of organs including the liver, kidney and heart. However, the transgene is not active despite transduction of heart cells (cardiomyocytes) by AAV9. Viral transduction can be verified by monitoring green fluorescent protein (GFP) expression, which is absent in all transduced cells. Transgene expression is induced specifically upon intraperitoneal tamoxifen delivery, upon which GFP expression is induced, in specific cell types.

Example 1: In Vitro Validation

In developing this platform, the inventors first assessed the sensitivity of the AAV9 construct to Cre recombinase mediated GFP transgene induction. As shown in FIG. 1A (top panels), in the absence of Cre recombinase, GFP expression is not detected. In contrast, ectopic Cre recombinase expression driven by the myosin light chain 2v (MLC2v) promoter (Ht-AAV9) leads to expression of GFP in cardiomyocytes (FIG. 1A lower panels). The specificity of Cre recombinase-dependent GFP expression was further confirmed by immunoblotting with GFP specific antibodies and quantitative polymerase chain reaction (qPCR) (FIGS. 1B and 1C).

Example 2: In Vivo Validation

To demonstrate the utility of the system in vivo, the cardiomyocyte targeting AAV9-MLC2v-lox-STOP-GFP-transgene virus was injected intravenously into mice expressing tamoxifen-inducible Cre recombinase under the control of the cardiac-specific MHCα promoter. As shown in FIGS. 2A and 2B, control MHCα-Cre− mice did not exhibit GFP expression (FIG. 2A, upper panel and 2B), while mice harbouring the Cre recombinase transgene (MHCα-Cre+) expressed high levels of GFP upon tamoxifen delivery (FIG. 2A, lower panel and 2B) in cardiac ventricles. Transgene expression was observed in hearts of MHCα-Cre+ mice infected with AAV9-GFP at 10-20 weeks post-injection, but was absent in non-cardiac tissue throughout this duration.

Example 3: Use of a Plurality of Transcribable Units

To further exploit this transgene delivery platform for in vivo, in situ functional genomics screens, a human U6 RNA promoter (RNA PolIII-driven transcription) based system for the expression of multiple coding genes was developed, including non-coding RNAs (ncRNA), micro RNAs (miRNA), small interfering RNAs (siRNA), short-hairpin RNAs (shRNA) or a combination thereof within a single AAV, such that only one transgene or shRNA is expressed per cell of the target organ. Cell specific expression of the individual transgene or shRNA is achieved through combinatorial utilization of loxP elements in a convergent or divergent orientation as shown in FIG. 3A. In FIG. 3B, the minimal repetitive unit of the construct is shown.

Upon Cre recombinase expression in the target tissue, a series of excision and recombination events occur (FIGS. 4A and 4B) culminating in the presence of a single transgene downstream of the promoter amenable to transcription. Transcription of other transgenes further downstream is inhibited due to the presence of a T5 transcriptional stop motif leading to fall off of RNA Polymerase III after transcription of the transgene directly downstream of the promoter. In FIG. 5A-D, a simplified representation of events is shown for a number of larger transgene sets.

This system was successfully applied for expression of up to 50 individual shRNAs to target a total of 48 gene targets. Two shRNAs, positioned at the 5' and 3' ends, carry non-silencing shRNAs serving as controls to ensure specificity of the other shRNAs and to maintain some degree of targeted organ function. In FIG. 6, the percentage of cells within the heart expressing a specific transgene is shown for an AAV9 harbouring 10 (FIG. 6A), 20 (FIG. 6B) or 50 (FIG. 6C) shRNAs. The shRNAs contained within the respective cells were determined by qPCR and/or sequencing of RNA derived from enzymatically dissociated heart cells subjected to FACS sorting. As indicated in FIG. 6A-C, transgene expression is strongly correlated to its position within the AAV9 construct. Transgenes at the flanks are most heavily represented, while those positioned at the centre are least represented. However, in the context of the adult mouse heart, within a 50 transgene construct, the lowest expressed transgene was detected in approximately 0.2% of cardiomyocytes within the heart corresponding to roughly 40 000 heart cells.

Example 4: In Vivo Assessment of a Plurality of Transcribable Units for Phenotype Variation As an example for the in vivo assessment of gene function for phenotype variation using the current invention the study of fatty liver disease is detailed. Mice expressing Cre-recombinase in the liver were maintained on a high fat diet to induce fatty livers. Next, the mice were injected with a virus containing shRNAS targeting 50 individual genes that are hypothesised to effect fat accumulation in the liver. Thereafter, the liver was dissociated using standard methods yielding individual hepatocytes. Some of those hepatocytes carry a fat load while others do less so or haven't any fat load. Using a fat dye that enters and stains lipids accumulated in the hepatocytes can be sorted by fluorescense-activated cell sorting (FACS). This yields defined populations of cells containing varying amounts of fat based on the staining intensity. Knockdown of genes hypothesised to promote lipid accumulation would be predicted to inhibit lipid accumulation. Hence, selection of cell populations containing negligible amounts of the fat-dye and performing targeted sequencing (using unique primer specific for a sequence within the expression vector) or quantitative PCR (of all 50 shRNAs) of the cell, identifies shRNAs that prevented fat accumulation in these cells. In doing so, genes involved in fat accumulation in the liver are identified.

This method can be applied for other possible phenotypic readouts such as cell size, cell morphology, surface or internal protein expression, apoptosis, proliferation, etc. Basically any parameter that serves as readout for a gene function that can be distinguished by staining, size or cell morphology can be used.

Example 5: Novel Mouse System for In Vivo Orthotropic Identification of Disease-Associated Genes The invention can also be employed for the generation of a novel mouse system for in vivo orthotropic identification of disease-associated genes. This is achieved by introduction of multiple small interfering RNAs (siRNA), short hairpin RNAs (shRNA) or coding or non-coding genes flanked by a combination of two different loxP motifs (that are mutually exclusive but of similar Cre recombinase sensitivity and efficiency) into a single transgene at the mouse ROSA26 locus. This system enables the functional assessment of multiple genes in a single mouse, in a cell type and organ-specific manner.

The DNA construct shown in FIGS. 3A and 3B, where FIG. 3B represents the minimal modular unit of this system, while FIG. 3A depicts a schematic of the transgene, is introduced at the ROSA26 locus. Expression of the respective siRNAs in the transgene in FIG. 3A is tightly regulated by Cre recombinase activity (Cre) activity, such that in any given cell only one siRNA (or shRNA or coding or non-coding gene) is active. This occurs upon completion of Cre-mediated recombination as shown in FIGS. 4A and 4B, where the arrows represent the multiple routes taken to reach completion of Cre-activity in a three (FIG. 4A) or four (FIG. 4B) siRNA transgene.

Crossing mice carrying the multi-construct transgene at the ROSA26 locus with mice expressing Cre in an organ-specific manner, allows the relevance of specific genes in the context of disease to be assessed. Through siRNA/shRNA-mediated knockdown or ectopic expression of multiple genes in a cell-type specific manner, while simultaneously ensuring that only one gene or RNA is upregulated or inhibited in one cell, the function of multiple genes or RNAs can be addressed simultaneously in one mouse. Using this approach, the in vivo function of a protein family (consisting of 50 members) can be interrogated in a specific cell type with 1-3 mice as opposed to the 50 mice that would be required using conventional methods.

Upon derivation of mice carrying both the multi-transgene construct and a tissue-specific Cre, these mice can be subjected to pathologic stress stimuli to induce a disease state. The relevance of a specific siRNA (or shRNA, or coding or non-coding gene) will thereafter be assessed through a phenotypic screen.

Taking heart disease as a model, cell size in response to pathologic stress can be used as readout. Heart cells can be isolated using the established Langendorf method and fluorescence activated cell sorting (FACS) performed to distinguish large cells from small cells. Once the cell populations have been separated, parallel sequencing for siRNAs, shRNAs or genes enriched in the population of large or small cells can be determined. siRNAs enriched in the small cell population would be predicted to inhibit pathologic growth in response to stress. In doing so, the in vivo functional significance of a specific siRNA or gene can be determined. Other readouts such as cell proliferation, ROS levels, induction of specific protein, etc. can also be used using the same principle. This system can also be used without a stress stimulus to assess if siRNA-mediated gene inactivation or ectopic gene expression is sufficient to induce a disease phenotype.

Concept Behind Invention:

This novel system for large-scale in vivo organ-targeted mammalian transgenesis is applicable for the tissue specific and inducible expression of transgenes in a broad range of embryonic, newborn and adult animals. The use of this platform enables the high-throughput and economical gain-of-function and loss-of function assessment of coding and non-coding gene function in vivo in an organ-specific manner. Importantly, by facilitating the knockdown or ectopic expression of multiple genes/ncRNAs in a cell-type specific manner in one animal, while simultaneously ensuring that only one gene or RNA is upregulated or inhibited per cell, the function of multiple genes or ncRNAs can be addressed simultaneously. Using this approach, the in vivo function of a protein family (consisting of up to 50 members) can be interrogated in a particular cell type with several animals as opposed to the around 50 animals that would be required using conventional methods. Thereafter, function of specific transgenes can be addressed using functional or phenotypic readouts including apoptosis, cell proliferation, ROS levels, induction of specific protein, etc. followed by cost-effective targeted qPCR or sequencing techniques to identify phenotype-associated gene targets. This platform not only facilitates easy in vivo gene validation, but is also advantageous by reducing the number of animals used in experiments. This technology can be further extended for in vivo screening of DNA/RNA-based therapeutic compounds in rodents and non-rodent/large animals, for optimization of plant growth in agriculture and used in combination with CRISPR/Cas technology for simultaneous multi-loci genome editing for generation of mutations, knockouts or knock-ins in a single cell-specific manner for downstream functional genomic analysis.

This platform serves as the missing link for translation between animals and human clinical studies by facilitating the ability to cost-effectively and efficiently extend preliminary findings in small animal models to more physiologically relevant large animal models such as the pig, sheep and non-human primate, prior to targeted therapies in humans.

The invention claimed is:

1. An in vivo method for determining phenotype alteration by a plurality of transcribable units in a non-human tissue of interest comprising the steps of:
(A) administering to a non-human tissue of interest in vivo,
a DNA expression vector comprising, in 5' to 3' orientation, a plurality of recombination units, wherein a single recombination unit comprises at least one transcribable unit and a first and second target site both recognizable by a site-specific recombinase, wherein said non-human tissue of interest expresses a site-specific recombinase,
(B) harvesting the tissue of interest,
(C) separating said tissue of interest into individual cells and sorting said individual cells according to phenotype of interest,
(D) identifying said transcribable unit(s) expressed in each of said sorted individual cells; and
(E) assaying for the altered phenotype that results from expression of the transcriptional unit(s) in said individual cells, wherein
- (i) recombination can only occur between two target sites of the same type, said first target site is located at the 5' start site of said recombination unit and said second target site is located at the 3' end of said recombination unit, and
- (ii) for all recombination unites comprised within said DNA vector, the orientation of all of said first target sites are the same, and the orientation of all of said second target sites are the same.

2. The method according to claim 1, wherein said phenotype of interest is characterized by a cell size, a cell morphology, a cell staining or a cell marker.

3. The method according to claim 1, wherein said plurality of recombination units comprises 2 to 80 recombination units.

4. The method according to claim 1, wherein each of said recombination units in said DNA vector additionally comprises a transcriptional terminator located between the transcribable unit closest to the 3' end of said recombination unit and said second type of target site.

5. The method according to claim 1, wherein said site-specific recombinase is selected from Cre-recombinase and FLP.

6. The method according to claim 1, wherein said DNA vector comprises a multitude of selection units, wherein each of said selection units comprises:
   a promoter to enable expression of the transcribable units, and
   a multitude of recombination units.

7. The method according to claim 1, wherein said DNA expression vector is a viral vector derived from a virus selected from the group consisting of adeno-associated virus, adenovirus, lentivirus, retrovirus, and baculovirus.

8. The method of claim 3, wherein said plurality of recombination units comprises 5 to 60 recombination units.

9. The method of claim 3, wherein said plurality of recombination units comprises 10 to 50 recombination units.

10. The method of claim 6, wherein the promoter to enable expression of the transcribable units is a U6 promoter.

* * * * *

SEQUENCE LISTING

```
<160> NUMBER OF SEQ ID NOS: 5

<210> SEQ ID NO 1
<211> LENGTH: 34
<212> TYPE: DNA
<213> ORGANISM: Bacteriophage P1

<400> SEQUENCE: 1
ataacttcgt atagcataca ttatacgaag ttat                              34

<210> SEQ ID NO 2
<211> LENGTH: 34
<212> TYPE: DNA
<213> ORGANISM: Artificial Sequence
<220> FEATURE:
<223> OTHER INFORMATION: loxP-2722 mutant

<400> SEQUENCE: 2
ataacttcgt ataggatact ttatacgaag ttat                              34

<210> SEQ ID NO 3
<211> LENGTH: 35
<212> TYPE: DNA
<213> ORGANISM: Artificial Sequence
<220> FEATURE:
<223> OTHER INFORMATION: mutated FRT site

<400> SEQUENCE: 3
tgaagttcct atactttcta gagaatagga acttc                             35

<210> SEQ ID NO 4
```

```
<211> LENGTH: 35
<212> TYPE: DNA
<213> ORGANISM: Saccharomyces cerevisiae

<400> SEQUENCE: 4
gaagttccta ttctctagaa agtataggaa cttca                                35

<210> SEQ ID NO 5
<211> LENGTH: 1299
<212> TYPE: DNA
<213> ORGANISM: Artificial Sequence
<220> FEATURE:
<223> OTHER INFORMATION: codon optimized version of S.cerevisae FLP
      according to Raymond, C. S., & Soriano, P. (2007). High-Efficiency
      FLP and ?C31 Site-Specific Recombination in Mammalian Cells. PLoS
      ONE, 2(1), e162

<400> SEQUENCE: 5
atggctccta agaagaagag gaaggtgatg agccagttcg acatcctgtg caagaccccc      60
cccaaggtgc tggtgcggca gttcgtggag agattcgaga ggcccagcgg cgagaagatc     120
gccagctgtg ccgccgagct gacctacctg tgctggatga tcacccacaa cggcaccgcc     180
atcaagaggg ccaccttcat gagctacaac accatcatca gcaacagcct gagcttcgac     240
atcgtgaaca agagcctgca gttcaagtac aagacccaga aggccaccat cctggaggcc     300
agcctgaaga agctgatccc cgcctgggag ttcaccatca tcccttacaa cggccagaag     360
caccagagcg acatcaccga catcgtgtcc agcctgcagc tgcagttcga gagcagcgag     420
gaggccgaca agggcaacag ccacagcaag aagatgctga aggccctgct gtccgagggc     480
gagagcatct gggagatcac cgagaagatc ctgaacagct tcgagtacac cagcaggttc     540
accaagacca gaccctgta ccagttcctg ttcctggcca cattcatcaa ctgcggcagg     600
ttcagcgaca tcaagaacgt ggaccccaag agcttcaagc tggtgcagaa caagtacctg     660
ggcgtgatca ttcagtgcct ggtgaccgag accaagacaa gcgtgtccag gcacatctac     720
tttttcagcg ccagaggcag gatcgacccc ctggtgtacc tggacgagtt cctgaggaac     780
agcgagcccg tgctgaagag agtgaacagg accggcaaca gcagcagcaa caagcaggag     840
taccagctgc tgaaggacaa cctggtgcgc agctacaaca aggccctgaa gaagaacgcc     900
ccctacccca tcttcgctat caagaacggc cctaagagcc acatcggcag gcacctgatg     960
accagctttc tgagcatgaa gggcctgacc gagctgacaa acgtggtggg caactggagc    1020
gacaagaggg cctccgccgt ggccaggacc acctacaccc accagatcac cgccatcccc    1080
gaccactact tcgccctggt gtccaggtac tacgcctacg accccatcag caaggagatg    1140
atcgccctga aggacgagac caaccccatc gaggagtggc agcacatcga gcagctgaag    1200
ggcagcgccg agggcagcat cagatacccc gcctggaacg gcatcatcag ccaggaggtg    1260
ctggactacc tgagcagcta catcaacagg cggatctga                           1299
```